United States Patent [19]

Nix et al.

[11] 4,394,445
[45] Jul. 19, 1983

[54] ENZYMATIC GLYCERIDE HYDROLYSIS

[76] Inventors: Paul T. Nix, 62 Forest Dr., Jackson, N.J. 08527; Janet M. Santoro, 70 Kingsly Way, Freehold, N.J. 07728; Joyce E. Stephens, P.O. Box 51, Avon-by-Sea, N.J. 07717

[21] Appl. No.: 331,449

[22] Filed: Dec. 15, 1981

Related U.S. Application Data

[63] Continuation of Ser. No. 187,664, Sep. 16, 1980, abandoned, and a continuation of Ser. No. 13,862, Feb. 22, 1979, abandoned.

[51] Int. Cl.³ ............................................. C12Q 1/44
[52] U.S. Cl. ...................................... 435/19; 435/198
[58] Field of Search ..................... 435/19, 198, 20, 21, 435/876, 939

[56] References Cited

U.S. PATENT DOCUMENTS

| 3,431,175 | 3/1969 | Arima et al. | 435/198 |
| 3,513,073 | 5/1970 | Maurernay et al. | 435/198 |
| 3,703,591 | 11/1972 | Bucolo et al. | 435/19 X |
| 3,759,793 | 9/1973 | Stork et al. | 435/19 X |
| 3,862,009 | 1/1975 | Wahlefeld et al. | 435/19 X |
| 4,056,442 | 11/1977 | Huang et al. | 435/19 X |
| 4,066,508 | 1/1978 | Rauscher et al. | 435/19 X |
| 4,168,203 | 9/1979 | Takahashi et al. | 435/19 X |

FOREIGN PATENT DOCUMENTS 1441642  7/1976  United Kingdom ............... 435/19

OTHER PUBLICATIONS

"Technicon Method No. SG4-0023PC6," 3/76, Technicon Instruments Corp.

Primary Examiner—Thomas G. Wyse
Attorney, Agent, or Firm—David Prashker

[57] ABSTRACT

A new stable combination of *Rhizopus arrhizus* lipase and *Pseudomonas fluorescens* lipase for hydrolyzing triglycerides to free glycerol in body fluids is disclosed. Substantially complete and rapid hydrolysis is provided by a mixture of enzymes using a ratio between 2:1 and 10:1, about 5:1 being preferred, the amounts representing units of activity of each lipase. Approximately 150 units of total lipases will provide substantially complete hydrolysis of the triglycerides contained in 20 microliters of serum up to a minimum concentration of 5 g./l. within 2.5 minutes at 37° C.

9 Claims, No Drawings

ENZYMATIC GLYCERIDE HYDROLYSIS

This application is a continuation of application Ser. No. 187,664 filed Sept. 16, 1980, abandoned, and a continuation of application Ser. No. 013,862 filed Feb. 22, 1979, abandoned.

BACKGROUND OF THE INVENTION

This invention relates to the in vitro clinical determination of glycerol esters in body fluids, and more particularly to the hydrolysis of glycerides to glycerol for analysis.

Glyceride concentration, particularly triglycerides in the body fluids of man and other animals, are known to be significant to a number of pathological conditions and its determination is a common clinical procedure. Generally, the glycerides are hydrolyzed and the glycerol thus freed is assayed by a variety of techniques. Hydrolysis by both chemical and enzymatic means are known, with the latter being generally preferred for safety, specificity and convenience. A number of single source lipases have been proposed, for example, *Rhizopus arrhizus* lipase (hereinafter LIPR) in U.S. Pat. No. 3,759,793, and *Pseudomonas fluorescens* lipase (hereinafter LPL) in Chimica Chimica Acta, 81 (1977) 125:130. However, such single source lipases either will not fully hydrolyze glycerides or will do so only under limited conditions or with impractically large amounts of enzyme or time. Thus, so far as known, such single source lipases are not used. Instead, mixtures of enzymes are employed, for example, LIPR with protease as disclosed in U.S. Pat. No. 3,708,591; mixtures of LIPR and carboxylesterase as disclosed in U.S. Pat. No. 3,862,009; and mixtures of LIPR with *Candida cylindracea* as disclosed in U.S. Pat. No. 4,056,442. Such mixtures also have limitations, however. Proteases limit stability of the reagent since they eventually attack protein in the reagent or sample, carboxyleasterases are difficult to purify, and combinations of LIPR and *Candida cyclindracea* lipases are inhibited by wetting agents commonly used in reagents, samples or controls, especially in automated, continuous flow analyzers.

Automated continuous flow analyzers impose important limitations on conditions for hydrolyzing triglycerides. Frequently calibrators and standards contain surfactants, while use of small samples and short reaction times are common. For example, the Technicon SMAC instrument provides a fixed incubation time of 2.5 minutes at 37° C., and employs surfactants in its calibrating standards which inhibit some lipases, for example the mixture disclosed in U.S. Pat. No. 4,056,442.

Following hydrolysis of triglyercides, the glycerol freed may be assayed by any suitable procedure. The glycerol kinase procedure is commonly used and is described in a number of publications, including U.S. Pat. Nos. 3,703,591; 3,759,793; and 4,056,442 and the Technicon Instruments Corporation publication dated March, 1976, entitled "Technicon Method No. SG4-0023PC6. These disclosures are herein incorporated by reference.

In one procedure, the assay reactions are summarized as follows:

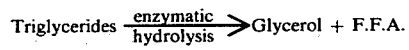
Triglycerides $\xrightarrow{\text{enzymatic hydrolysis}}$ Glycerol + F.F.A.

Glycerol + ATP $\xrightarrow{GK}$ GP + ADP

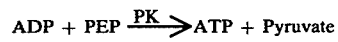
ADP + PEP $\xrightarrow{PK}$ ATP + Pyruvate

Pyruvate + NADH $\xrightarrow{LDH}$ Lactate + NAD

As used above, FFA=free fatty acids; ATP=adenosine triphosphate; GK=glycerol kinase; GP=glycerol phosphate; ADP—adenosine diphosphate; PEP=phosphoenolpyruvic acid; LDH=lactate dehydrogenase; PK=pyruvate kinase; NAD and NADH=Nicotinamide adenine dinucleotide, oxidized and reduced. NADH absorbs at 340 nm while NAD does not, the decrease in optical absorbance at 340 nm being measured and calibrated as a measure of the concentration of triglycerides in the sample. Methods which measure the reduction of NAD by other enzymatic means are also known and are described for example in U.S. Pat. No. 4,056,442 and in Clinica Chimica Acta, 81 (1977) 125:130. These disclosures are also incorporated herein by reference.

SUMMARY OF THE INVENTION

According to the present invention, a novel mixture of lipases has been found which are stable and which will fully hydrolyze trigercides in body fluids in the short times available in continuous flow analyzers and in the presence of surfactants. This mixture is useable in manual or other procedures, but is especially adapted for rapid, continuous flow instrumental assay. Following hydrolysis therewith, any suitable procedure is employed to assay the released glycerol, for example, the glycerol kinase, NADH/NAD procedure described above.

The novel mixture comprises a mixture of *Rhizopus arrhizus* lipase (LIPR) and *Pseudomonas fluorescens* lipase (LPL) in the ratio of units/milliliter of each lipase between about 2:1 and about 10:1, more preferably between about 4:1 and 10:1, and most preferably about 5:1. Thus the mixture, per hundred units of total lipase, should comprise between about 65 and 91 units LIPR and 35 to 9 units LPL. Sufficient total lipase to hydrolyze the sample within the available time should be employed. For rapidly hydrolyzing about 20 microliters of test sample containing up to 5 grams per liter or more of triglyceride, about 150 units of total lipase should be employed. A mixture of 250 u/ml *Rhizopus arrhizus* lipase and 50 u/ml *Pseudomonas fluorescens* lipase is preferred. The mixture should be buffered to a pH between about 6.0 and 7.0, more preferably 6.4 to 6.5, and is preferably lyophilized for stability or prepared as a dry powder.

DETAILED DESCRIPTION OF THE INVENTION

*Rhizopus arrhizus* lipase (E.C. 3.1.1.3) is described in the foregoing publications and one method for its preparation is disclosed in U.S. Pat. No. 3,513,073. *Pseudomonas fluorescens* lipase and methods for its preparation are disclosed in U.S. Pat. No. 3,431,175 and in Clinica Chimica Acta, 81 (1977) 125:130. Both are commercially available and the organisms are on deposit in recognized collections. A unit of lipase activity as used herein is the amount of fatty acid neutralized by one micromole of sodium hydroxide in one minute at 25° C. at pH 8.

The preferred hydrolyzing lipase mixture according to the present invention is an aqueous solution shown in Example 1 below. It is preferably supplied in dry or dried form for stability in storage and is reconstituted with distilled water prior to use.

EXAMPLE 1

| Lipase u/ml | |
|---|---|
| LIPR | ≧250 |
| LPL | ≧50 |
| Potassium phosphate, mM/l. | 90 |
| Bovine serum albumin, g./l. | 3.8 |
| pH | 6.5 |

For use in a continuous flow instrument such as the Technicon SMAC instrument having a fixed incubation or reaction time of 2.5 minutes at 37° C., a serum sample is diluted 1:6 by volume with distilled water containing a small quantity of surfactant, e.g., 0.1% Triton X-100 (DuPont), and 4.25 parts by volume of the reconstituted lipase reagent is added to each part of diluted sample. 118 ul of diluted sample is used in the above identified instrument and about 0.4 ml of lipase reagent added per test. Complete hydrolysis is obtained in 2.5 minutes.

Comparative tests were run in a continuous flow Technicon instrument with a fixed 2.5 minute reaction time (37° C.) using (1) the aqueous reagent of Example 1 and (2) the standard enzyme mixtures supplied by the Technicon Instrument Corporation comprising a mixture of LIPR and protease as described in U.S. Pat. No. 3,703,591. Good correlation was obtained as illustrated by the typical results shown in Table I below wherein the results given are in mg/dl. triglycerides.

TABLE I

| Sample | Example 1 | Expected Values |
|---|---|---|
| 1 | 103 | 100 |
| 2 | 269 | 266 |
| 3 | 574 | — |
| 4 | 138 | 133 |
| 5 | 90 | 82 |
| 6 | 135 | 131 |
| 7 | 284 | 270 |
| 8 | 577 | 565 |

Samples 1-8 are patient sera where triglyceride concentrations were measured after effecting hydrolysis using the preferred lipase formulation of Example 1 on a Technicon SMAC instrument, and where the Expected Value of each serum was determined using a commercial lipase reagent based on U.S. Pat. No. 3,703,951. Correlation of these sera show that the surfactants used in the instrument calibration did not inhibit the lipase reaction. In each test, glycerol freed by hydrolysis was dialyzed into a flowing stream of assay reagent using the NADH to NAD reactions described above, the resulting change in absorbance being read optically at 340 nm and calibrated to triglyceride concentration in sample.

A preferred free glycerol reagent mixture is given in Example 2 below, the amounts given being per aqueous liter.

EXAMPLE 2

| I. Glycerol Kinase Reagent: | |
|---|---|
| GK, units | ≧2610 |
| Triethylamine hydrochloride mM | 100 |
| II. Glycerol Substrate Reagent: | |

-continued

| TRIS buffer, mM | 32 |
|---|---|
| Magnesium sulfate, mM | 8.6 |
| ATP, mM | 8.6 |
| PEP, mM | .306 |
| NADH, mM | .273 |
| LDH, units | ≧2400 |
| PK, units | ≧1200 |

These reagents were employed in obtaining the EXAMPLE 1 results reported in TABLE 1. For extended storage, typical ionic and protein stabilizers can be added. Technicon Instrument Corporation commercial reagents were used to obtain the results reported under Expected Values.

Further test have indicated that neither LIPR or LPL alone will fully hydrolyze triglyercides in sample or calibrant within 2.5 minutes incubation time at 37° C. and that the present combination is synergistic. Longer times and temperatures from about room temperature up to about 50° C. may be used, if desired. Sufficient total enzyme within the above ratios should be used to provide full hydrolysis within the time available and the range of concentrations to be assayed.

It should be understood that the foregoing description is for the purpose of illustration and that the present invention includes all equivalents and modifications within the scope of the appended claims.

What is claimed is:

1. A composition useful for the hydrolysis of a glycerol ester in an aqueous medium comprising a mixture of from about 65 to 91 units of *Rhizopus arrhizus* lipase and from about 35 to 9 units of *Pseudomonas fluorescens* lipase per 100 units of total lipase.

2. A composition according to claim 1 wherein the ratio of *Rhizopus arrhizus* lipase to *Pseudomonas fluorescens* lipase is between about 2:1 and 10:1.

3. A composition according to claim 2 wherein the ratio is about 5:1.

4. A composition according to claim 1 in an aqueous medium buffered to a pH between about 6.0 and 7.0 and containing at least about 300 units total lipase per milliliter.

5. A dried composition according to claim 4.

6. A reagent composition for determining triglyceride concentration in serum by hydrolyzing triglycerides to glycerol and free fatty acids and measuring the light absorbance of an aqueous fluid containing the hydrolyzed glycerol which comprises an enzyme mixture according to claim 1 together with chemical means for effecting an absorbance change of said aqueous fluid proportional to the amount of glycerol released in the serum.

7. A reagent composition for determining triglyceride concentration in serum by hydrolyzing triglycerides present therein to glycerol and measuring the light absorbance of an aqueous fluid containing said glycerol which comprises a dried enzyme mixture according to claim 5, including chemical means for effecting an absorbance change of said aqueous fluid proportional to the amount of glycerol released in the serum.

8. A reagent composition according to claim 7 wherein said chemical means comprises glycerolkinase, adenosine triphosphate, phosphoenol pyruvic acid, NADH, lactate dehydrogenase and pyruvate kinase.

9. The method for hydrolyzing a glycerol ester and for determining the amount of glycerol ester present in an aqueous body fluid which comprises incubating said fluid with a mixture of enzymes according to claim 1 or 4 for a time less than about ten minutes to fully hydrolyze said glycerol ester and determining the amount of glycerol or fatty acid released by the hydrolysis.

* * * * *